United States Patent
Cole

(10) Patent No.: US 6,238,417 B1
(45) Date of Patent: May 29, 2001

(54) METHOD FOR FIXING AT LEAST TWO BONE SEGMENTS

(76) Inventor: J. Dean Cole, 500 Lakeview Dr., Orlando, FL (US) 32804

( * ) Notice: Subject to any disclaimer, the term of this patent is extended or adjusted under 35 U.S.C. 154(b) by 0 days.

(21) Appl. No.: 09/471,062

(22) Filed: Dec. 22, 1999

Related U.S. Application Data

(62) Division of application No. 09/070,332, filed on Apr. 30, 1998, now Pat. No. 6,019,762.

(51) Int. Cl.[7] .................................................. A61B 17/08
(52) U.S. Cl. ............................................................. 606/213
(58) Field of Search ................................. 606/65, 66, 73, 606/213, 217, 218

(56) References Cited

U.S. PATENT DOCUMENTS

| | | | |
|---|---|---|---|
| 2,398,915 | * 4/1946 | Bell | 606/59 |
| 2,485,531 | * 10/1949 | Dzus et al. | 606/73 |
| 4,456,005 | * 6/1984 | Lichty | 606/60 |
| 4,640,271 | * 2/1987 | Lower | 606/105 |
| 4,688,561 | * 8/1987 | Reese | 606/64 |
| 4,796,612 | * 1/1989 | Reese | 606/72 |
| 4,869,242 | * 9/1989 | Galluzzo | 606/59 |
| 4,940,467 | * 7/1990 | Tronzo | 606/66 |
| 4,976,712 | * 12/1990 | VanderSlik | 606/59 |

* cited by examiner

Primary Examiner—Gene Mancene
Assistant Examiner—Eduardo C. Robert
(74) Attorney, Agent, or Firm—Woodard, Emhardt, Naughton, Moriarty & McNett

(57) ABSTRACT

The invention relates to an adjustable length fixation device having a head slidable along the shaft of the fixation device. The head is larger than the shaft and prevents further distal migration of the shaft and may preferably include an external surface for engaging bone to prevent proximal migration of the shaft. The head includes an engagement portion which may be deformed to securely engage the shaft to prevent removal of the head from the shaft. The invention also contemplates a method of insertion which includes inserting the shaft into the bone, sliding the head along the shaft and into engagement with the bone, securely engaging the head to the shaft, and severing the shaft proximal of the head to thereby form a fastener of the required length.

19 Claims, 11 Drawing Sheets

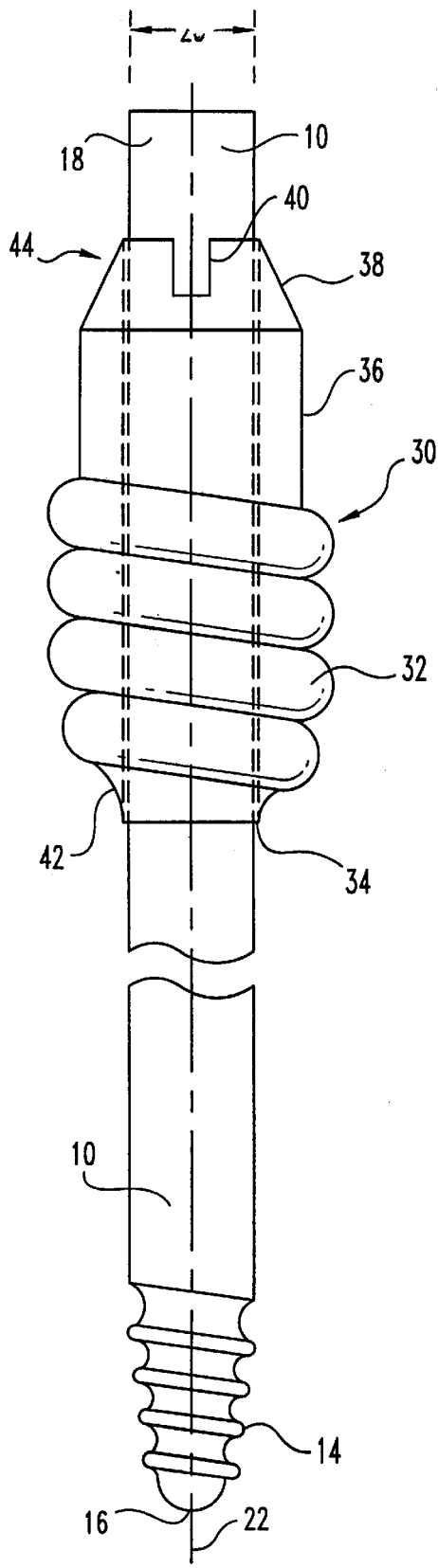
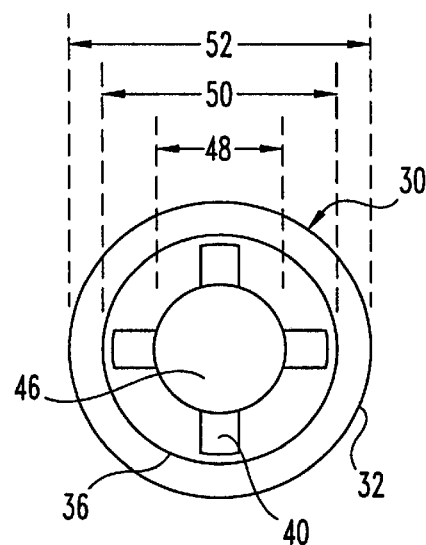
Fig. 1
Fig. 2

METHOD FOR FIXING AT LEAST TWO BONE SEGMENTS

REFERENCE TO RELATED APPLICATION

This is a divisional application of U.S. patent application Ser. No. 09/070,332 filed Apr. 30, 1998 is now U.S. Pat. No. 6,019,762.

BACKGROUND OF THE INVENTION

This invention relates generally to surgical devices for fixation of two or more segments of tissue, and more particularly to a fixation device useful for securing two or more segments of bone in a desired spatial relation.

The use of both internal and external fixation devices to prevent major movement between two or more sections of bone is well known in the art. External casts and braces have commonly been employed to prevent movement between larger bone segments, and have been particularly useful in the fixation of long bone fractures in the extremities. For small bone segments and bones within the trunk of the body which may not be readily immobilized by braces and casts; plates, screws, nails, and wires have been implanted to maintain the relative position of these bones during the healing process. In some instances, a single screw with a uniform shaft is screwed between two bone segments to maintain these in place. Alternatively, a pinning device such as a nail may be driven into both of the bone segments to create fixation. In other applications, a lag screw is utilized with a first threaded portion passed through a first bone segment and threaded into a second segment of bone. A nut is then threaded onto a second machine threaded portion of the lag screw to reduce the fracture between the two bone fragments. Alternatively, a similar type of lag screw may be utilized in conjunction with a plate. Each of a series of lag screws is inserted into bone fragments and a plate is attached across the machine threaded portion of the lag screw. A nut is threaded onto each screw thereby attaching the plate to the bone and maintaining the spatial relationship of the bone fragments.

For smaller bones and bone fragments, small wires, commonly known as Kirschner wires (K-wires), have been inserted into the bone to immobilize the fragments. After the wires are inserted, the proximal section of the wire is cut to the desired length. While these devices have been generally successful, at least initially, in accomplishing the desired immobilization, there are a number of problems which have been encountered with their use. Specifically, it has been found that in some instances, the fixation wire can migrate from the point of its initial insertion leading to loss of fracture fixation or damage to surrounding bodily structures, such as nerves or blood vessels adjacent the entry or exit site of the wire. Moreover, cutting the wire can result in a wire end that may be sharp, leading to possible tissue irritation adjacent the wire. In an effort to limit migration of the wire, the cut end may be bent over or left protruding from the skin, also leading to possible tissue irritation and/or infection. Additionally, if the wire is trimmed too close to the bone and the wire migrates inward, the end could be lost well within the bone surface, making it impossible to retrieve without damaging the surrounding bone structure. Thus, there remains a need for an orthopedic fixation device having the beneficial affects of the above-referenced devices but offering ease of insertion, patient comfort after insertion, reduced chances for infection, and the ability to withdraw the device after a desired time period.

SUMMARY OF THE INVENTION

The present invention relates to an adjustable length fixation device comprising an elongated shaft and a head fixable to the shaft. The head includes an internal channel with an engaging portion movable between a first position and a second position. When the engaging portion is in the first position, the internal channel defines a first configuration adapted to slidingly receive the elongated shaft. When the engageable portion is in a second position, the internal channel defines a second configuration adapted to prevent movement of the head along the elongated shaft.

The present invention also contemplates a method for fixing two tissue segments. The method comprises providing an elongated shaft having a proximal end and a distal end, and a head having a channel for slidably receiving the elongated shaft. The elongated shaft distal end is inserted through a first tissue segment and into a second tissue segment. The head is positioned about the proximal end of the shaft and slidingly advanced along the shaft toward its distal end. The head is positioned adjacent the first tissue segment and locked to the shaft.

An apparatus according to the present invention further contemplates an instrument for removing a head from an adjustable length fixation device. The removal instrument comprises an outer member having a longitudinal axis and defining a longitudinally extending internal channel. The internal channel includes an anvil surface. An inner tube is sized to be received within the internal channel and includes a longitudinally extending cutting blade. The blade is disposed adjacent the anvil and upon rotation of the inner member in relation to the outer member, the blade is urged toward the anvil to cut a head disposed between the blade and anvil.

The present invention further contemplates an orthopedic fixation system including a plate in combination with an adjustable length fixation device according to the present invention. A fixation plate having at least one aperture, may be placed along the tissue to be fixed. An elongated shaft may extend through the aperture in the plate and into the tissue to be fixed. A head having an outer surface for engagement with the plate and an internal channel, is positioned on the shaft with the shaft extending through the internal channel. The head may then slide along the shaft until it engages the plate and is fixed in position to engage the plate and the shaft. In one preferred embodiment, the head includes a series of external threads to mate with a similar internal thread pattern in the plate. In another preferred embodiment, the aperture of the plate includes at least a partially spheroidal surface which is engaged by a corresponding surface on the head to permit non-perpendicular orientation of the shaft with respect to the plate.

One object of the present invention is to provide an adjustable fixation device. Another object of the present invention is to provide a K-wire fixation device with a head slidable along the shaft. A further object of the present invention is to provide a method for fixation of two or more bone segments with an elongated shaft and an adjustable head. Yet a further object of the invention is to provide a plate and adjustable length fixation device, the fixation device having angular freedom of movement with respect to an opening in the plate. Still a further object is the provision of an instrument to remove a head locked to a shaft according to the present invention. These and other objects of the present invention will become apparent to those skilled in the art, based on the following description.

BRIEF DESCRIPTION OF THE DRAWINGS

FIG. 1 is a side view of the adjustable length fixation device in accordance with the present invention.

FIG. 2 is a top view of the fixation device of FIG. 1.

DESCRIPTION OF THE PREFERRED EMBODIMENTS

Figure 3:
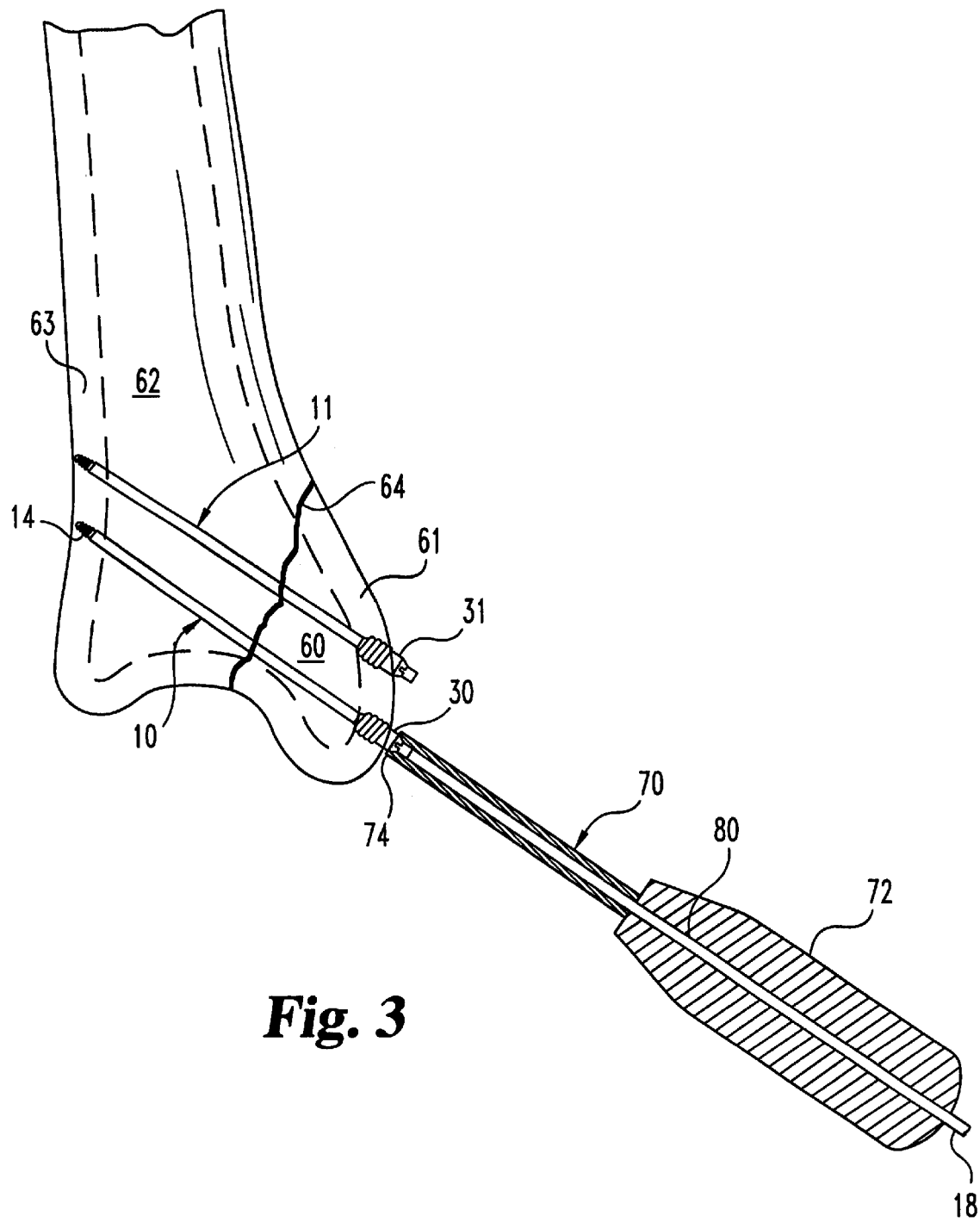
FIG. 3 is a partial cross-sectional view showing insertion of the fixation device of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

An adjustable length fixation device according to the present invention, is shown in FIG. 1. The fixation device includes an elongated shaft 10 having a proximal end 18 and a distal end 16. Adjacent distal end 16 is externally threaded portion 14. Elongated shaft 10 has a diameter 20 which extends over substantially the entire length of the elongated shaft. While the present invention is shown having a uniform diameter along the entire length of the elongated shaft 10, it is contemplated that the shaft could include varying diameters depending on the application in the body and the tool used to drive the shaft into position. In the preferred embodiment, elongated shaft 10 includes a longitudinal axis 22 which extends from the proximal end to the distal end.

In the embodiment of FIG. 1, threaded area 14 is shown having a diameter less than or equal to the diameter 20 of the entire shaft. Although this is shown in a preferred embodiment, it should be understood that the shaft may have a bayonet point, a trocar point, or a threaded portion 14 formed such that the threads have a diameter greater than diameter 20. Moreover, while threads are shown as a bone engaging surface on shaft 10, it is contemplated that the shaft may be smooth or utilize other bone engaging surfaces, such as ridges, knurling, barbs, etc. Additionally, the bone engaging surface could extend over a much longer segment of elongated shaft 10.

Referring now to FIGS. 1 and 2, there is shown a fixation device head 30 in accordance with the present invention. In a preferred embodiment of the present invention, head 30 is a ferrule including a series of external threads 32 adjacent distal end 34. Threads 32 terminate adjacent distal end 34 in a taper 42. Head 30 has a proximal end 44 with a taper 38 connected to the threads 32 by a crimping zone 36. In a preferred embodiment, crimping zone 36 is substantially cylindrical. However, it is contemplated that the crimping zone could be formed in a variety of shapes including, but not limited to, cylindrical, conical, triangular, rectangular, hexagonal, or any other geometric shape desired by the user. It will be understood that these shapes could be utilized by a driving tool to drive the head into the bone or for subsequent removal. In a preferred embodiment of head 30, slots 40 are formed within tapered area 38 to receive a corresponding driving tool. A driving tool (FIG. 3) may engage slots 40 to thread head 30 into surrounding bone. An additional feature of the present invention, is that threads 32 of head 30 and threads 14 of shaft 10 have substantially identical pitches. Thus, once head 30 has been joined with shaft 10, rotation of the shaft advances or withdraws the head and shaft in unison. While the use of substantially identical thread pitches is shown in a preferred embodiment, it is contemplated that the pitch of the threads adjacent the head and those adjacent the distal end of the shaft could be formed such that threads have different pitches. With threads of different pitches, rotation of shaft 10 with head 30 fixed thereto, may tend to compress a fracture line.

Head 30 further includes a substantially cylindrical internal channel 46 having a diameter 48. The diameter 48 is slightly larger than diameter 20 of shaft 10 to permit head 30 to slide freely along shaft 10. Channel 46 includes a deformable portion within crimping zone 36. It will be understood that diameter 48 may be altered by deforming the ferrule, particularly within crimping zone 36. It will be understood that the crimping may deform the internal channel 48 from the substantially cylindrical shape shown, to an irregular shape engaging shaft 10. The exterior surface of crimping zone 36 has a diameter 50. The outermost diameter 52 of threads 32 is larger than the crimping zone diameter 50. While this arrangement of diameters is shown in the preferred embodiment, it is contemplated that it may be desirable to have the diameter of crimping zone 36 larger than the diameter of threads 52 to prevent over insertion of the device into the bone.

Referring now to FIG. 3, a shaft 11 is shown inserted into a first bone fragment 60 and a second bone fragment 62 across fracture 64. A head 31, identical to head 30 of FIGS. 1 and 2, has been crimped to the proximal portion of shaft 11 and the proximal portion of shaft 11 removed.

Elongated shaft 10 is similarly shown inserted into first bone segment 60 and second bone segment 62 fracture 64. An insertion tool 70 is shown engaging head 30. Insertion tool 70 includes a cannula 80 adapted to receive shaft 10 along its entire length and allow the proximal end 19 of shaft 10 to extend beyond insertion tool 70. Insertion tool 70 includes a handle 72 which may be gripped by the user to transmit both rotational and compressive force to head 30.

Figure 4:
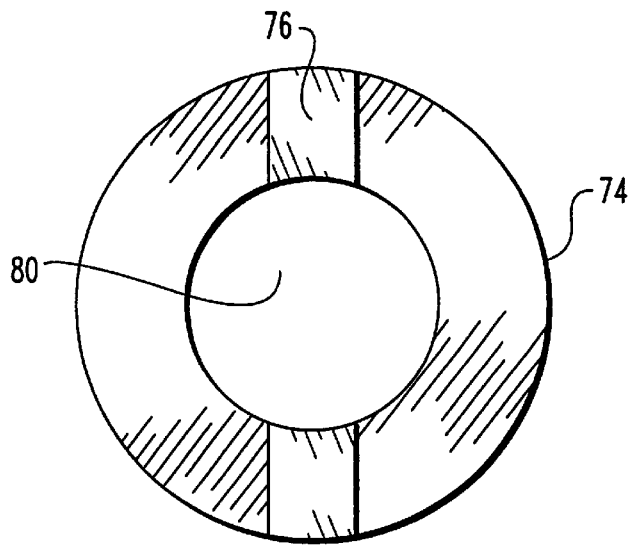
FIG. 4 is a partial end view of an insertion device.
Figure 5:
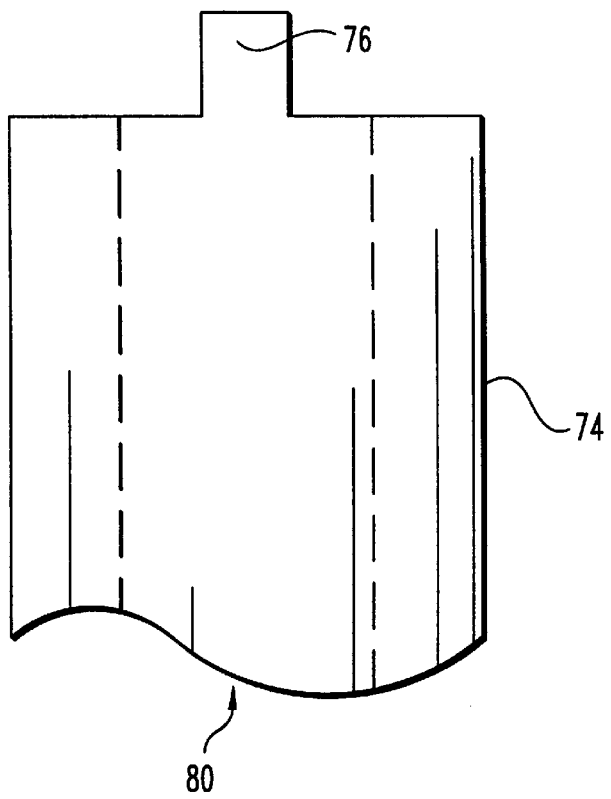
FIG. 5 is a partial side view of the insertion device of FIG. 4.

Insertion tool 70 has a driving end 74 adapted to engage proximal end 44 of head 30 to transmit rotational and compressive force to head 30. Referring now to FIGS. 4 and 5, the driving end 74 of insertion tool 70 includes projection 76 sized to be received within slots 40 of head 30.

Head 30 may be locked to shaft 10 by deforming at least a portion of the ferrule to engage shaft 10 and prevent movement of head 30 along shaft 10. In a preferred embodiment of the present invention, crimping is performed by a longitudinally extending crimping tool 90 as disclosed in U.S. application Ser. No. 09/013,434, which is incorporated herein by reference. While the description of the preferred embodiment discloses use of a longitudinal crimping tool, use of conventional crimping tools is within the scope and spirit of the present invention. Moreover, although a portion of head 30 is shown as being moveable to a locked position by deformation, it is contemplated that other locking mechanisms on head 30 may be utilized to hold shaft 10.

Figure 6:
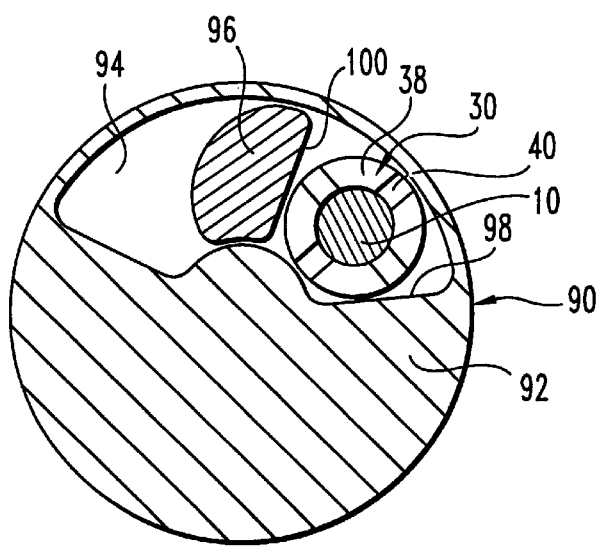
FIG. 6 is a cross-sectional view of the device of FIG. 1 surrounded by a crimping device.

As shown in FIG. 6, longitudinal crimping tool 90 is positioned over shaft 10 and head 30. Longitudinal crimping tool 90 includes an outer member 92 defining an interior channel 94. Shaft 10 and head 30 are positioned within interior channel 94. Additionally extending within interior channel 94 is an inner crimping member 96. Inner crimping member 96 includes a crimping surface 100. Outer member 90 includes a crimping surface 98 defined within inner channel 94. Although both crimping surfaces 98 and 100 are shown as substantially planar, it is contemplated that the surfaces could be formed of other cooperating configurations to provide alternative crimping patterns.

Figure 7:
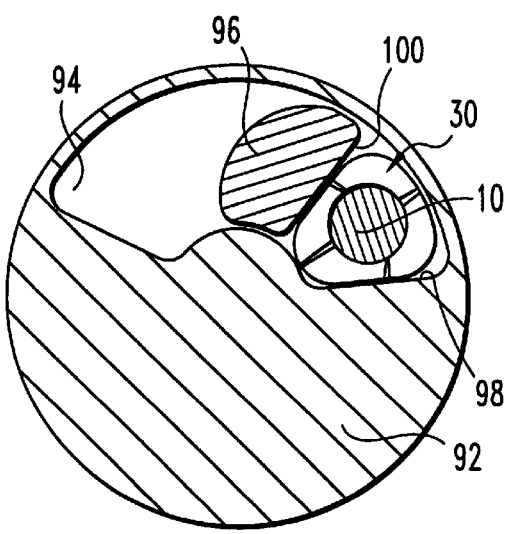
FIG. 7 is a cross-sectional view showing the crimping device engaging the fixation device of FIG. 1.

Referring now to FIG. 7, inner member 96 is moved in relation to outer member 92 to force crimping surfaces 100 and 98 toward one another. Movement of inner member 96 and outer member 92 deforms at least a portion of head 30 and in a preferred embodiment, a portion of shaft 10. In this manner, head 30 may lockingly engage shaft 10 to prevent further sliding movement along the longitudinal axis of shaft 10.

Figure 8:
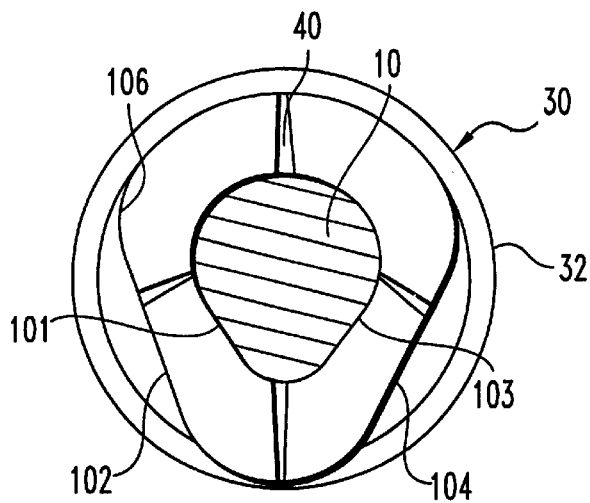
FIG. 8 is a cross-sectional view of the fixation device of FIG. 1 after crimping.

Referring now to FIG. 8, head 30 now includes a first planar surface 102 and a second planar surface 104 on the crimping zone of the device above the threaded area 32. Additionally, shaft 10 has been slightly deformed to create substantially planar surfaces 101 and 103 corresponding to surfaces 102 and 104, respectively. It will be understood that engagement of surfaces 101 and 103 with head 30 permit rotational force applied to head 30 to be effectively transmitted to shaft 10. Deformation of shaft 10 may be enhanced by forming the shaft of a softer material than the ferrule. A portion of slots 40 have now been deformed, thus inhibiting further use of insertion tool 70.

Figure 9:
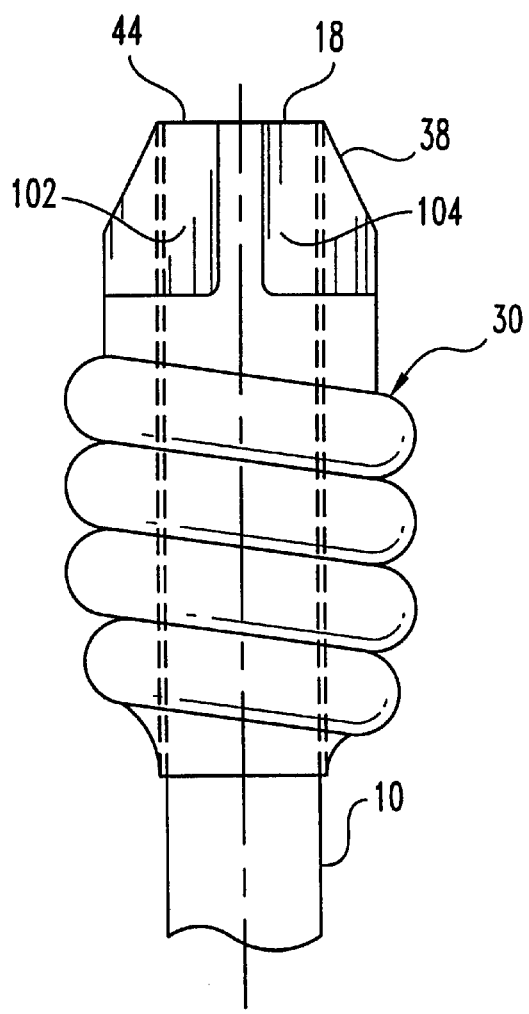
FIG. 9 is a side view of the fixation device of FIG. 1 after crimping and cutting.
Figure 10:
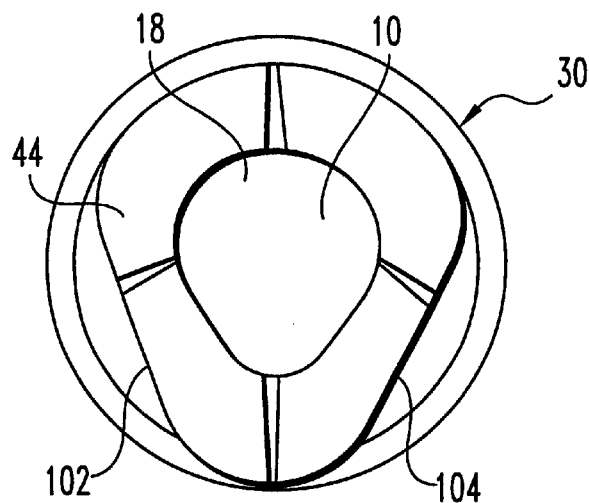
FIG. 10 is a top view of the device of FIG. 9.

Referring now to FIGS. 9 and 10, the interconnected head 30 and shaft 10 are cut within taper 38 to remove the proximally extending portion of head 30 and shaft 10. As shown in FIG. 9, proximal end 44 of head 30 and the proximal end 18 of shaft 10 are now co-terminous and substantially co-planar. The head and shaft have been severed within taper 38 to provide a smoother transition at the proximal end to avoid tissue irritation that might be caused by a sharp corner.

Figure 11:
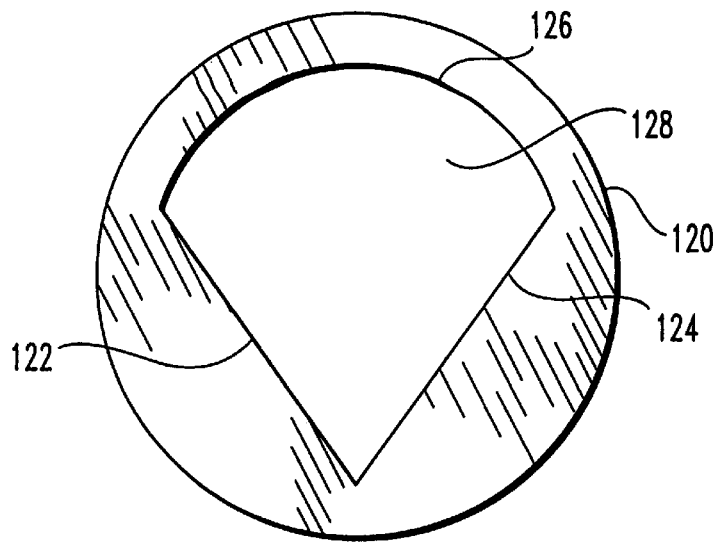
FIG. 11 is an end view of a socket of a removal tool.
Figure 12:
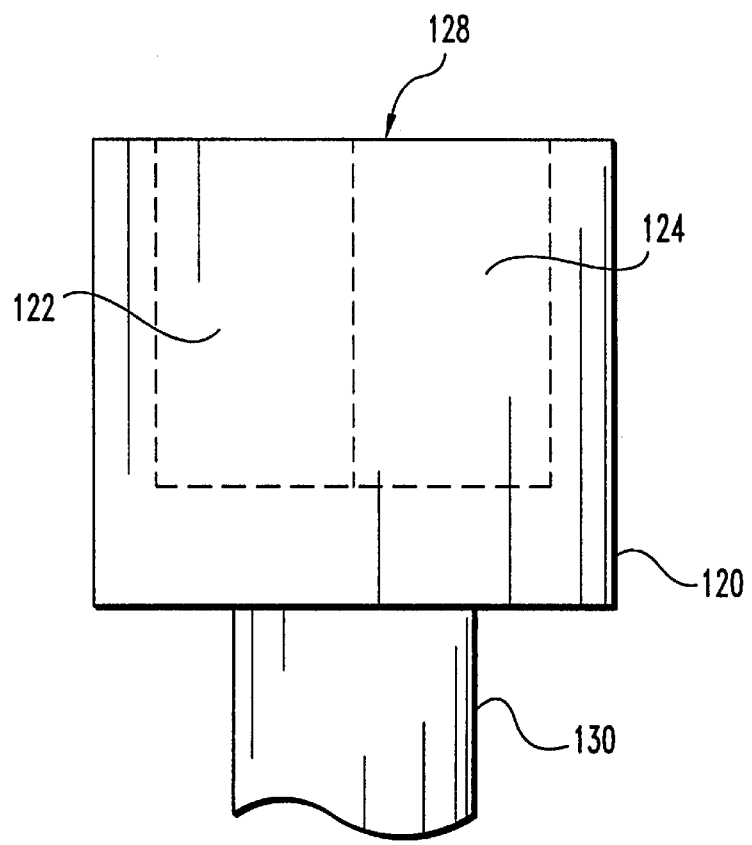
FIG. 12 is a partial side view of the socket of FIG. 11.

Referring now to FIGS. 11 and 12, there is shown a removal socket 120 for engaging the crimped head 30 of FIG. 9 for additional driving or removal of the device. Socket 120 includes interior socket 128 defining planar surfaces 122 and 124 and arcuate surface 126. It will be understood that socket 128 is sized to engage crimped head 30 with planar surfaces 124 and 122 engaging planar surfaces 102 and 104, respectively.

Figure 13:
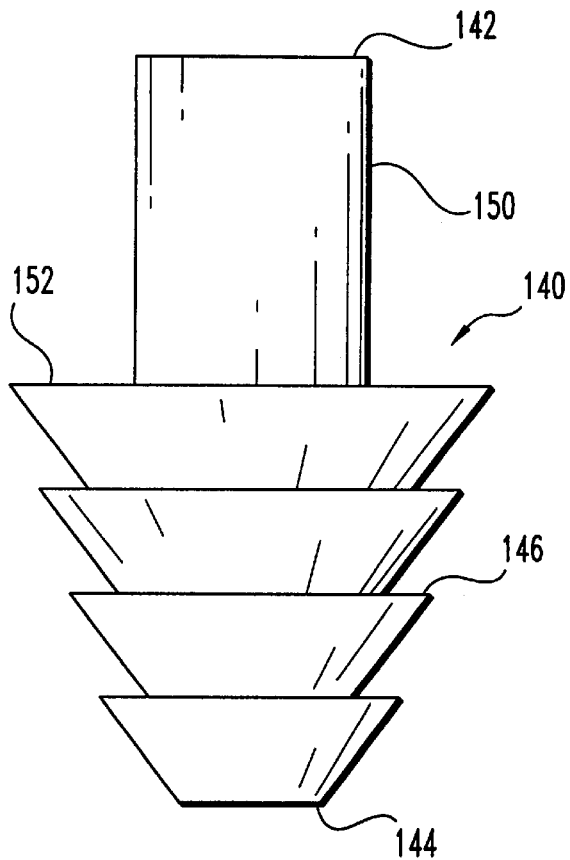
FIG. 13 is a side view of an alternative embodiment of a head according to the present invention.
Figure 14:
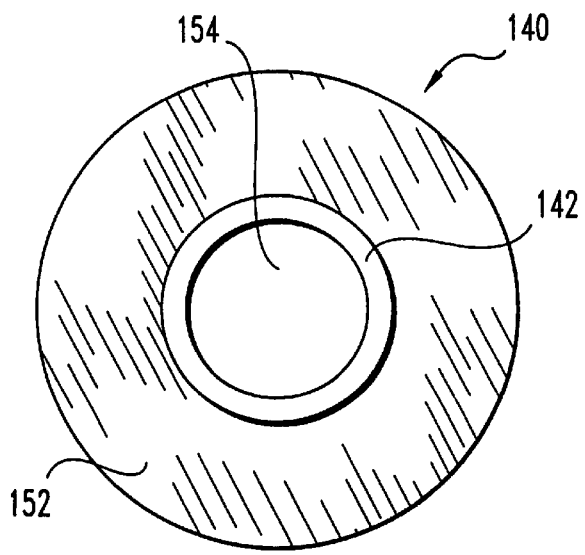
FIG. 14 is a top view of the head of FIG. 13.

Referring now to FIGS. 13 and 14, there is shown an alternative embodiment of a head 140, according to the present invention. Head 140 includes a distal end 144 and a proximal end 142. Adjacent distal end 144 are a series of graduated conical rings 146 adapted to engage surrounding bone upon insertion. Extending between rings 146 and proximal end 142 is a crimping and cutting zone 150. The proximal end of rings 146 further includes a shoulder 152 which may be used by an insertion tool to apply force to head 140 to slide it along shaft 10 and urge head 140 into surrounding bone.

Referring now to FIG. 3, in operation, shaft 10 is inserted into a first bone segment 60 and a second bone segment 62 across fracture line 64, such that threads 14 adjacent distal end 16 secure and engage at least a portion of the second bone segment 62. In many applications, it is desirable that threads 14 engage at least a portion of the harder cortical bone 63 of bone segment 62. Insertion of an elongated shaft in this manner is well known in the art and will not be further explained. With the proximal end 18 of shaft 10 extending well beyond the bone, head 30 is positioned over the proximal end 18 of shaft 10 and moved along the shaft towards distal end 16. Insertion tool 70 is likewise passed over proximal end 18 of shaft 10 and advanced along the shaft 10 until it is adjacent head 30. The driving end 74 of insertion tool 70 is then rotated until projection 76 is received in one of the slots 40. Once projection 76 has been securely seated in a slot 40, insertion tool 70 is rotated to advance threads 32 into the bone of first segment 62. It will be understood that for most applications, threads 32 are adapted to engage the harder cortical bone 61. Once head 30 has been inserted to the desired depth, insertion tool 70 is removed from shaft 10.

With head 30 inserted into bone segment 62 as desired, head 30 is then joined to shaft 10. In a preferred embodiment, a crimping tool is utilized to deform head 30 in crimping zone 36 to secure and engage shaft 10. While a longitudinally extending crimping tool has been described in a preferred embodiment, it is contemplated that any type of crimping tool may be utilized to perform the desired engaging function. Moreover, in a preferred embodiment, the crimping tool creates at least two planar surfaces for subsequent engagement by a driving/removal socket 120 (FIGS. 11 and 12). Once head 30 has been securely locked to shaft 10, a cutting device (not shown) is positioned adjacent tapered surface 38. The cutting tool (not shown) is operated to sever a portion of head 30 and shaft 10 extending proximal of the engagement point. In the preferred embodiment, both a portion of head 30 and shaft 10 are cut to provide a substantially co-terminous and co-planar surface on the proximal end to limit tissue irritation surrounding the protruding head and shaft. While severing of both the head and the shaft is disclosed in the preferred embodiment, it is contemplated that it is within the scope and spirit of the invention that only the shaft may be severed.

As an alternate method, shaft 10 may be inserted into the bone until it approaches a final location. Head 30 may be locked to shaft 10 and the head and shaft combination driven into a final position as an integral unit.

The device of the present invention may be removed by use of a socket 120 (FIGS. 11 and 12) positioned over the proximal end 44 of head 30. It will be understood that the planar surfaces 124 and 122 engage planar 102 and 104, respectively, to transmit rotational force to the head which is also transmitted to the shaft by means of the crimping engagement, to rotate the head and shaft to remove the device from bone segments 62 and 64.

Figure 15A:
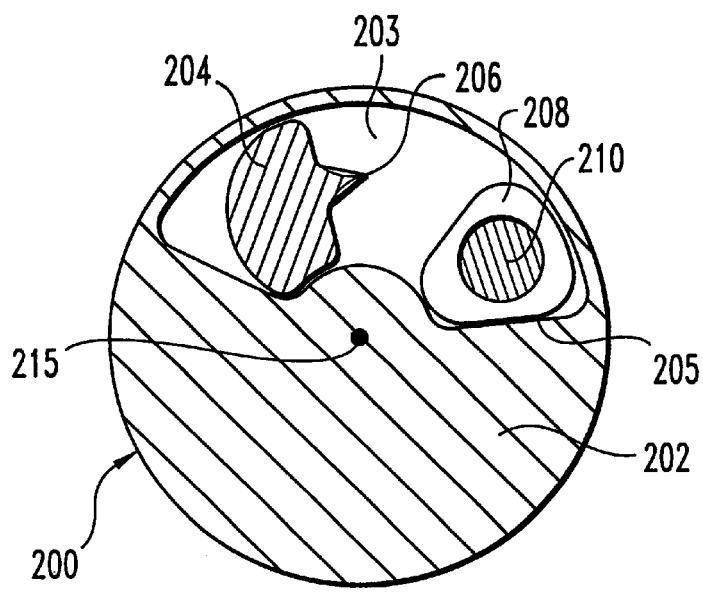
FIG. 15(a) is a cross-sectional end view of a head removal instrument according to the present invention.
Figure 15B:
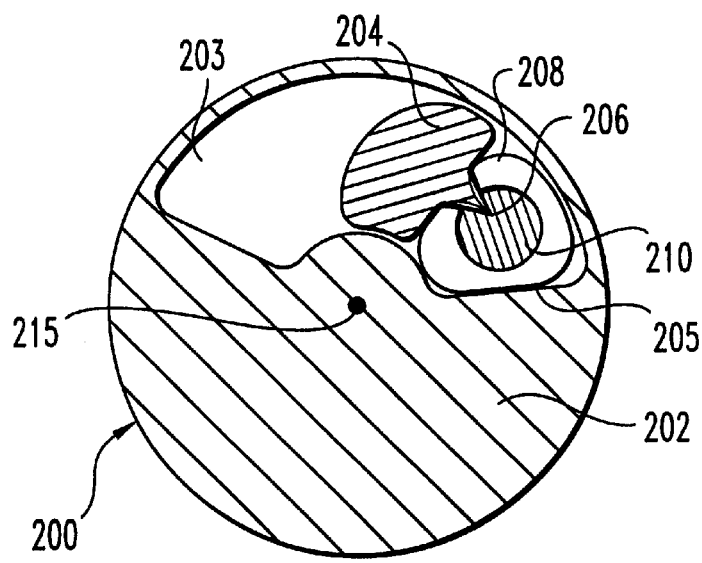
FIG. 15(b) is an end view of the removal instrument of FIG. 15(a) with the cutting blade engaging the head.

Referring now to FIGS. 15(*a*) and (*b*), there is shown an instrument for removing the head affixed to the shaft of an adjustable length fixation device according to the present invention. The removal instrument 200 includes an outer member 202 which defines an internal channel 203 that extends along longitudinal axis 215. As with the crimping tool previously disclosed, the combination of an outer member and movable inner member is more fully disclosed in U.S. application Ser. No. 09/013,434 which is incorporated herein by reference. In this embodiment, outer member 202 further includes anvil surface 205 defined within internal channel 203. Inner member 204 is disposed within internal channel 203 and extends along longitudinal axis 215 of outer member 202. Inner member 204 defines a cutting blade 206 which extends longitudinally along at least a portion of the axis of inner member 204. As shown in FIG. 15(*b*), inner member 204 may be moved in a rotational manner about longitudinal axis 215 within internal channel 203 to urge cutting blade 206 toward anvil 205. With shaft 210 and inner connected head 208 positioned adjacent anvil 205, cutting blade 206 may be urged toward anvil 205 to penetrate head 208, thereby cutting it away from shaft 210. Once head 208 has been severed by cutting blade 206, it may be more easily removed from the shaft for subsequent removal of the entire shaft.

Figure 16:
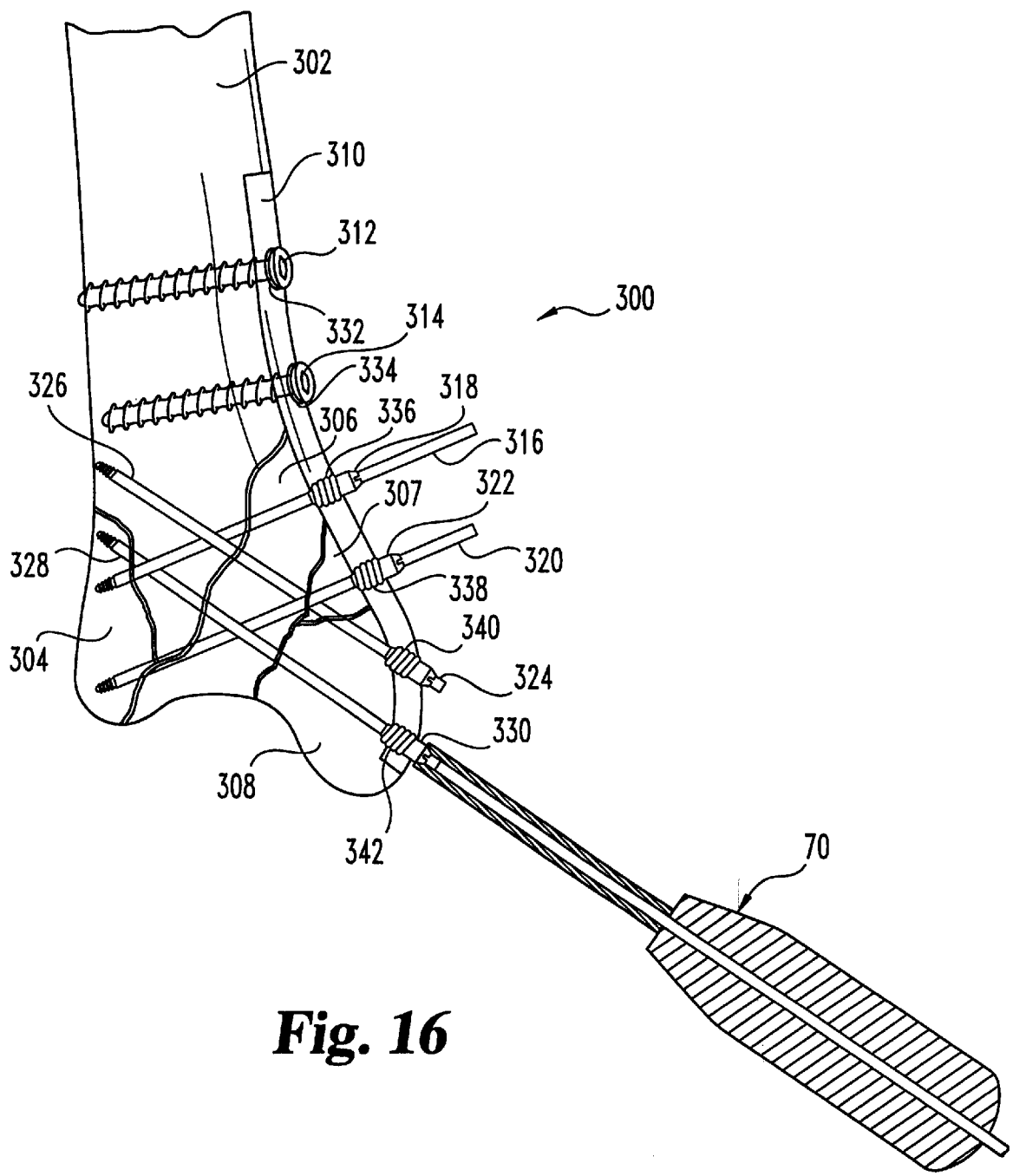
FIG. 16 is a partial cross-sectional view showing insertion of a fixation system in accordance with the present invention.

Referring now to FIG. 16, there is shown an orthopedic fixation system according to the present invention. While the fixation system may have a number of uses, it is particularly useful in immobilizing small bone fragments and joining them to a plate. More specifically, the system includes a plate 310 having a number of apertures therethrough to receive bone engaging members. As shown in FIG. 16, bone screws 312 and 314 extend through apertures 332 and 334, respectively, to engage the large bone segment 302. It will be understood that the use of conventional screws through the plate provides a solid fixation point for the plate, permitting the portion extending over the plurality of smaller bone fragments to rely on the bone screw fixation for greater stability of the device. K-wires 316 and 320 are positioned through apertures 336 and 338, respectively. K-wire 316 extends through bone segments 306, 302, and 304. K-wire 316 is joined to plate 310 by head 318. In a similar manner, shaft 320 extends through aperture 338 and plate 310 and into bone segments 307, 306, and 304. Head 322 joins shaft 320 to plate 310. In a similar manner, shafts 326 and 328 extend through apertures 340 and 252, respectively, and into the bone framents, and the shafts 326 and 328 are joined to plate 310 by heads 324 and 330, respectively. Tool 70, further described with reference to FIG. 3, may be used to insert the heads.

Figure 17B:
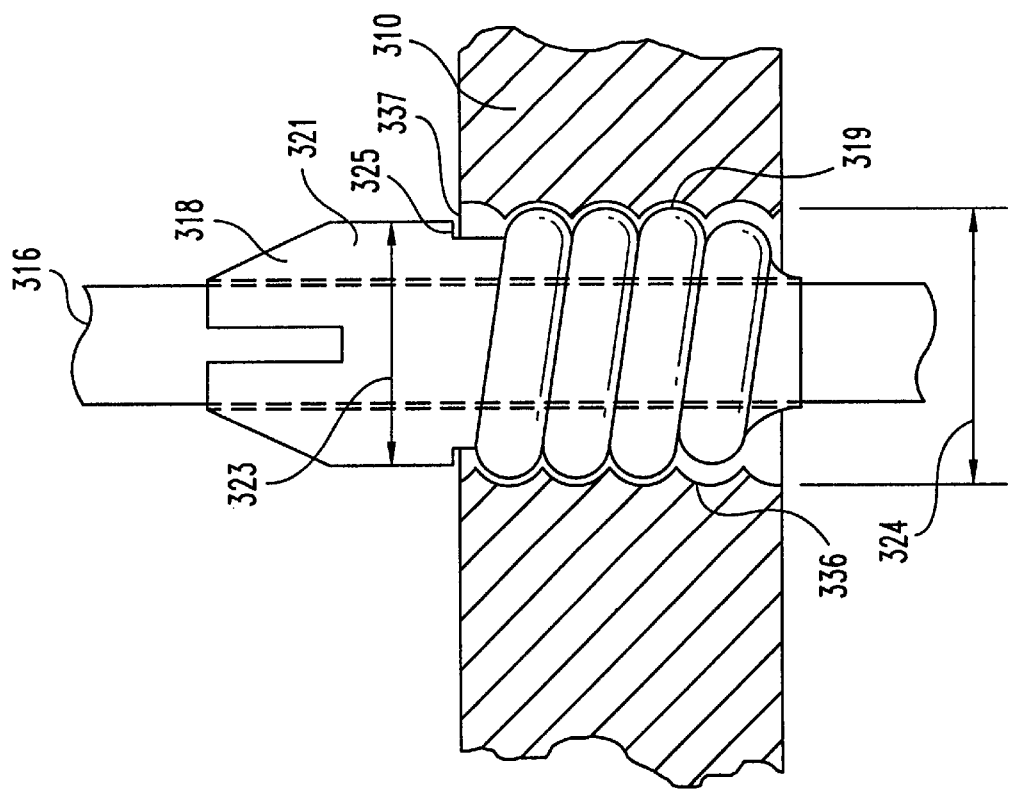
FIG. 17(b) is a partial cross-sectional view of an alternative embodiment of a head in engagement with a plate.
Figure 17A:
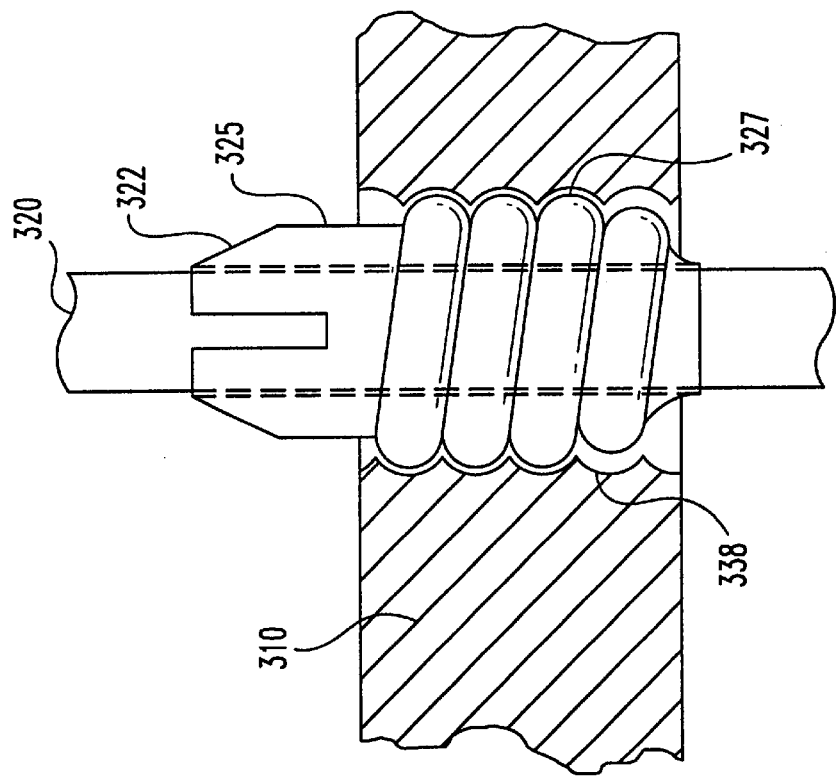
FIG. 17(a) is a partial cross-sectional view of a head in engagement with a plate.

Referring now to FIG. 17(*a*), there is shown a partial cross-sectional view of plate 310 with internally threaded aperture 338. Shaft 320 extends through aperture 338 and is interconnected to plate 310 by head 322. Head 322 includes an externally threaded portion 327 which engages the internally threaded opening 336. As previously described with other embodiments of this invention, head 322 may be joined to shaft 320 by deformation of the head in crimping area 325. Referring now to FIG. 17(*b*), shaft 316 extends through internally threaded aperture 336. Head 318 joins shaft 316 to plate 310 by engagement of externally threaded portion 319 with internally threaded opening 336. Head 318 includes an enlarged crimping area 321 having a diameter 323 larger than the minimum diameter 324 of opening 336. Thus, movement of head 318 is limited by the enlarged crimping area 321 when shoulder 325 engages plate surface 337 adjacent opening 336.

Figure 18:
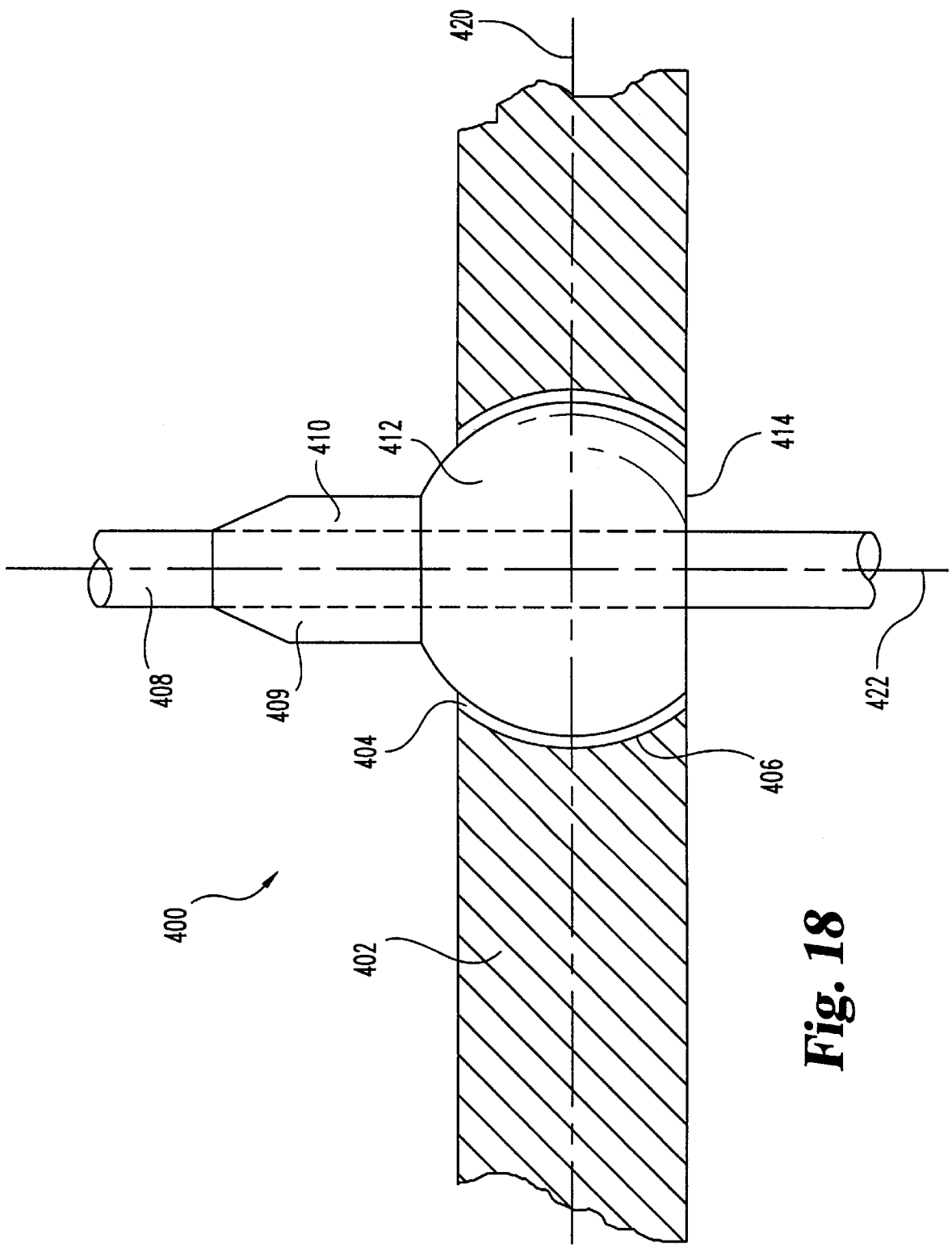
FIG. 18 is a partial cross-sectional view of a further embodiment of a head in engagement with a plate.

Referring now to FIG. 18, there is shown a plate and head combination permitting non-perpendicular alignment between shaft 408 and plate 402. Specifically, plate 402 includes an opening 404 having a partially spheroidal surface 406. In a similar fashion, head 409 includes a partially spheroidal portion 412 which extends into plate 402 and engages surface 406. As with the previous embodiments, head 409 may be joined to shaft 408 by deformation of the crimping area 410. As will be understood by those skilled in the art, engagement of portion 412 within opening 406 permits the longitudinal axis 422 of shaft 408 to extend in a variety of angular relations with respect to longitudinal axis 420 of plate 402. In a perpendicular relationship, surface 414 is in alignment with the bottom surface of plate 402. It will be understood that the combination of partially spheroidal opening 406 in plate 402 and partially spheroidal shaped body portion 412 on head 409, enhances the uses of the plate since the fixation shaft 408 does not have to extend directly perpendicular to the plate surface. While these two structures are shown in a preferred embodiment, it is contemplated that other structures could be utilized either in the plate, in the head, or in a plate-head combination, to provide a plurality of angular relationships between shaft 408 and plate 402.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for fixing at least two bone segments, comprising:
   providing an elongated shaft having a proximal portion and a distal portion, and a head having a channel for slidably receiving at least the proximal portion of said shaft;
   inserting the shaft distal portion through a first bone segment and into a second bone segment;
   positioning the head about the proximal portion of the shaft, the shaft extending through the channel in the head;
   sliding the head along the shaft toward the distal end;
   positioning the head adjacent the first bone segment; and
   locking the head to the shaft to prevent movement of the head towards either the proximal portion or the distal portion of the shaft.

2. The method of claim 1, wherein locking the head includes deforming at least a portion of the head.

3. The method of claim 2, wherein deforming the head further includes creating an external tool engagement surface adapted for cooperation with a removal tool.

4. The method of claim 3, wherein said deforming creates a substantially triangular shape with at least two planar engagement surfaces.

5. The method of claim 1, wherein the head includes a driving surface and further including the step of driving at least a portion of the head into the first bone segment.

6. The method of claim 5, wherein the head includes an external thread and said driving includes rotating the head to engage the threads with the first bone segment.

7. The method of claim 1, further including cutting the shaft adjacent the head to remove a proximal portion of the shaft.

8. The method of claim 7, wherein said head includes a proximal portion and said cutting includes cutting through the proximal portion of said head, wherein the remaining proximal end of the shaft and the remaining proximal end of the head are substantially co-planar.

9. The method of claim 1, wherein at least the distal end of the shaft is threaded and said inserting includes rotating the shaft to drive the threads into the second bone segment.

10. The method of claim 1, wherein the first and second bone segments include a cancellous portion and a cortical portion, and said inserting includes urging the shaft through the bone segments until the distal end engages the cortical portion of the second bone segment and then sliding the head down the shaft until the head engages the cortical portion of the first bone segment.

11. A method for fixing at least two tissue segments, comprising:

providing an elongated shaft having a proximal portion and a distal portion, and a head having a channel for slidably receiving at least the proximal portion of the shaft, wherein the head includes a proximal portion;

inserting the shaft distal portion through a first tissue segment and into a second tissue segment;

positioning the head about the proximal portion of the shaft, the shaft extending through the channel in the head;

sliding the head along the shaft toward the distal end;

positioning the head adjacent the first tissue segment;

locking the head to the shaft; and cutting the shaft adjacent the head to remove the proximal portion of the shaft, said cutting including cutting through the proximal portion of the head, wherein the remaining proximal end of the shaft and the remaining proximal end of the head are substantially co-planar.

12. The method of claim 11, wherein said locking the head includes deforming at least a portion of the head.

13. The method of claim 12, wherein said deforming the head further includes creating an external tool engagement surface adapted for cooperation with a removal tool.

14. The method of claim 13, wherein said deforming creates a substantially triangular shape with at least two planar engagement surfaces.

15. The method of claim 11, wherein the head includes a driving surface and further including driving at least a portion of the head into the first tissue segment.

16. The method of claim 15, wherein the head includes an external thread and said driving includes rotating the head to engage the threads with the first tissue segment.

17. The method of claim 11, wherein at least the distal end of the shaft is threaded and said inserting includes rotating the shaft to drive the threads into the second tissue segment.

18. The method of claim 11, wherein the first and second tissue segments are each bone and include a cancellous portion and a cortical portion, and said inserting includes urging the shaft through the bone until the distal end engages the cortical portion of the second bone and then sliding the head down the shaft until the head engages the cortical portion of the first bone.

19. A method for joining at least two bone segments, comprising:

providing an elongated shaft having a first periphery, a proximal portion, a distal portion and a longitudinal axis extending between the proximal and distal portions, and a head having an internal channel with a second periphery, the second periphery larger than the first periphery such that the head is freely slidable along the longitudinal axis of the shaft;

inserting the shaft distal portion through a first bone segment and into a second bone segment;

positioning the head about the proximal portion of the shaft, the shaft extending through the channel in the head;

sliding the head along the shaft toward the distal end;

securing the head to the shaft to prevent further movement of the head along the longitudinal axis of the shaft.

\* \* \* \* \*